(12) United States Patent
Polla

(10) Patent No.: US 7,572,817 B2
(45) Date of Patent: Aug. 11, 2009

(54) 2,5-DISUBSTITUTED 3-MERCAPTOPENTANOIC ACID

(75) Inventor: Magnus Polla, Mölndal (SE)

(73) Assignee: AstraZeneca AB, Sodertalje (SE)

( * ) Notice: Subject to any disclaimer, the term of this patent is extended or adjusted under 35 U.S.C. 154(b) by 543 days.

(21) Appl. No.: 10/517,713

(22) PCT Filed: Jun. 10, 2003

(86) PCT No.: PCT/SE03/00970

§ 371 (c)(1),
(2), (4) Date: Dec. 10, 2004

(87) PCT Pub. No.: WO03/106420

PCT Pub. Date: Dec. 24, 2003

(65) Prior Publication Data

US 2005/0176780 A1    Aug. 11, 2005

(30) Foreign Application Priority Data

Jun. 14, 2002   (SE) .................................. 0201837

(51) Int. Cl.
*A61K 31/44*    (2006.01)
*A61K 31/425*   (2006.01)
*A61K 31/38*    (2006.01)
*A61K 31/36*    (2006.01)
*C07D 217/00*   (2006.01)
*C07D 213/72*   (2006.01)
*C07D 207/00*   (2006.01)
*C07D 487/02*   (2006.01)
*C07D 277/00*   (2006.01)
*C07D 239/00*   (2006.01)
*C07D 241/04*   (2006.01)
*C07D 223/00*   (2006.01)

(52) U.S. Cl. ........................ 514/352; 514/370; 514/438; 514/464; 514/466; 546/139; 546/304; 548/190; 548/400; 548/453; 544/242; 544/358; 540/582

(58) Field of Classification Search ................. 514/352, 514/370, 412, 438, 464, 466; 546/304, 139; 548/190, 453, 400; 544/242, 358; 540/582
See application file for complete search history.

(56) References Cited

FOREIGN PATENT DOCUMENTS

WO    WO-00/66557    11/2000

*Primary Examiner*—Taylor Victor Oh
(74) *Attorney, Agent, or Firm*—Morgan Lewis & Bockius LLP

(57) ABSTRACT

The present invention concerns compounds of formula (I), and pharmaceutically acceptable salts or solvates thereof, or solvates of such salts, which compounds inhibit carboxypeptidase U and thus can be used in the prevention and treatment of diseases where inhibition of carboxypeptidase U is beneficial. In further aspects, the invention relates to compounds of the invention for use in therapy; to processes for preparation of such new compounds; to pharmaceutical compositions containing at least one compound of the invention, or a pharmaceutically acceptable salt or solvate thereof, as active ingredient; and to the use of the active compounds in the manufacture of medicaments for the medical use indicated above.

8 Claims, No Drawings

2,5-DISUBSTITUTED 3-MERCAPTOPENTANOIC ACID

RELATED APPLICATIONS

This application is a national stage filing under 35 U.S.C. 371 of International Application PCT/SE03/00970, filed Jun. 10, 2003, which claims priority from Sweden Application No. 0201837-2, filed Jun. 14, 2002 the specifications of each of which are incorporated by reference herein. International Application PCT/SE03/00970 was published under PCT Article 21(2) in English.

The present invention relates to novel compounds, and pharmaceutically acceptable salts thereof, which inhibit basic carboxypeptidase, more specifically carboxypeptidase U, and thus can be used in the prevention and treatment of diseases wherein inhibition of carboxypeptidase U is beneficial, such as thrombosis and hypercoagulability in blood and tissue, atherosclerosis, adhesions, dermal scarring, cancer, fibrotic conditions, inflammatory diseases and those conditions which benefit from maintaining or enhancing bradykinin levels in the body. In further aspects, the invention relates to compounds of the invention for use in therapy; to processes for preparation of such new compounds; to pharmaceutical compositions containing at least one compound of the invention, or a pharmaceutically acceptable salt thereof, as active ingredient; and to the use of the active compounds in the manufacture of medicaments for the medical use indicated above.

Fibrinolysis is the result of a series of enzymatic reactions resulting in the degradation of fibrin by plasmin. The activation of plasminogen is the central process in fibrinolysis. The cleavage of plasminogen to produce plasmin is accomplished by the plasminogen activators, tissue-type plasminogen activator (t-PA) or urokinase-type plasminogen activator (u-PA). Initial plasmin degradation of fibrin generates carboxy-terminal lysine residues that serve as high affinity binding sites for plasminogen. Since plasminogen bound to fibrin is much more readily activated to plasmin than free plasminogen this mechanism provides a positive feedback regulation of fibrinolysis.

One of the endogenous inhibitors to fibrinolysis is carboxypeptidase U (CPU). CPU is also known as plasma carboxypeptidase B, active thrombin activatable fibrinolysis inhibitor (TAFIa), carboxypeptidase R and inducible carboxypeptidase activity. CPU is formed during coagulation and fibrinolysis from its precursor proCPU by the action of proteolytic enzymes, such as thrombin, thrombin-thrombomodulin complex or plasmin. CPU cleaves basic amino acids at the carboxy-terminal of fibrin fragments. The loss of carboxy-terminal lysines and thereby of lysine binding sites for plasminogen then serves to inhibit fibrinolysis. By inhibiting the loss of lysine binding sites for plasminogen and thus increase the rate of plasmin formation, effective inhibitors of carboxypeptidase U are expected to facilitate fibrinolysis.

2-Mercaptomethyl-3-guanidinoethylthiopropanoic acid is reported as a carboxypeptidase N inhibitor. More recently, this compound has been shown to inhibit CPU, Hendriks, D. et al., Biochimica et Biophysica Acta, 1034 (1990) 86-92.

Guanidinoethylmercaptosuccinic acid is reported as a carboxypeptidase N inhibitor. More recently, this compound has been shown to inhibit CPU, Eaton, D. L., et al., The Journal of Biological Chemistry, 266 (1991) 21833-21838.

CPU inhibitors are disclosed in WO 00/66550, WO 00/66557, WO 03/013526 and WO 03/027128 and a pharmaceutical formulation containing a CPU inhibitor and a thrombin inhibitor is disclosed in WO 00/66152. Inhibitors of plasma carboxypeptidase B are disclosed in WO 01/19836. Inhibitors of TAFIa are disclosed in WO 02/14285.

It has now been found that compounds of formula (I) are particularly effective as inhibitors of carboxypeptidase U and are thereby useful as medicaments for the treatment or prophylaxis of conditions wherein inhibition of carboxypeptidase U is beneficial.

Thus, the present invention provides a compound of formula (I):

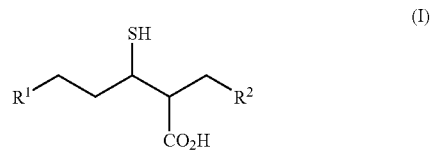

wherein:

$R^1$ is phenyl {optionally substituted by halogen, hydroxy, cyano, $C_{1-4}$ alkyl (itself optionally mono-substituted by cyano, hydroxy or phenyl), $C_{1-4}$ alkoxy (itself optionally substituted by tetrahydrofuranyl), $CF_3$, $OCF_3$, methylenedioxy, $C(O)R^3$, $S(O)_2R^4$, phenyl (itself optionally substituted by halogen), phenoxy (itself optionally substituted by halogen) or tetrahydrofuranlyoxy}, naphthyl, pyridinyl, 1,2,3,4-tetrahydropyrimidin-2,4-dione-yl (optionally substituted by $C_{1-4}$ alkyl) or tetrahydrothienyl;

$R^2$ is aminopyridinyl, aminothiazolyl or 3-azabicyclo[3.2.1] octyl;

$R^3$ is hydroxy, $C_{1-4}$ alkoxy (itself optionally substituted by phenyl (itself optionally substituted by halogen) or pyridinyl), $NR^5R^6$ or an N-linked 5- or 6-membered heterocyclic ring {unsubstituted or mono-substituted by hydroxy, oxo, $C_{1-4}$ alkyl (itself optionally substituted by hydroxy or NHphenyl), $CO_2(C_{1-4}$ alkyl) or phenyl (itself optionally substituted by halogen)};

$R^4$ is $NR^7R^8$ or an N-linked 5- or 6-membered heterocyclic ring {unsubstituted; mono-substituted by hydroxy, oxo, $C_{1-4}$ alkyl (itself optionally substituted by hydroxy or NHphenyl), $CO_2(C_{1-4}$alkyl) or phenyl (itself optionally substituted by halogen); or fused to a benzene ring which is optionally substituted by $C_{1-4}$ alkoxy};

$R^5$, $R^6$, $R^7$ and $R^8$ are, independently, hydrogen, $C_{1-4}$ alkyl {optionally substituted by halogen, cyano, hydroxy, phenyl (itself optionally substituted by halogen or methylenedioxy), pyridinyl, $CO_2H$ or $CO_2(C_{1-4}$alkyl)} or $C_{2-4}$ alkenyl;

provided that when $R^2$ is 6-aminopyridin-3-yl then $R^1$ is substituted phenyl, naphthyl, pyridinyl, 1,2,3,4-tetrahydropyrimidin-2,4-dione-yl (optionally substituted by $C_{1-4}$alkyl) or tetrahydrothienyl;

or a pharmaceutically acceptable salt or solvate thereof, or a solvate of such a salt.

The compounds of formula (I) exist in isomeric forms and the present invention covers all such forms and mixtures thereof in all proportions. Both the pure enantiomers, racemic mixtures and equal and unequal mixtures of two enatiomers are within the scope of the present invention. It should also be understood that all the diastereomeric forms possible are within the scope of the invention.

The term $C_{1-4}$ alkyl denotes a straight or branched alkyl group having 1 to 4 carbon atoms in the chain. Examples of alkyl include methyl, ethyl, n-propyl, iso-propyl, n-butyl, iso-butyl, sec-butyl and tert-butyl.

The term $C_{1-4}$ alkoxy denotes an alkyl-O-group, where alkyl is straight or branched chain and examples include methoxy and ethoxy.

Halogen includes fluoro, chloro, bromo and iodo (but is, for example, fluoro or chloro).

An N-linked 5- or 6-membered heterocyclic ring is, for example, a pyrrolidinyl, piperidinyl or piperazinyl ring.

In one particular aspect the present invention provides a compound of formula (I) wherein $R^1$ is phenyl {optionally substituted by halogen, hydroxy, cyano, $C_{1-4}$ alkyl (itself optionally mono-substituted by cyano or hydroxy), $C_{1-4}$ alkoxy, $CF_3$, $OCF_3$, methylenedioxy, $C(O)NH_2$, $S(O)_2NH_2$ or phenyl (itself optionally substituted by halogen)}, pyridinyl or tetrahydrothienyl; $R^2$ is aminopyridinyl, aminothiazolyl or 3-azabicyclo[3.2.1]octyl; provided that when $R^2$ is 6-aminopyridin-3-yl then $R^1$ is substituted phenyl, pyridinyl or tetrahydrothienyl; or a pharmaceutically acceptable salt or solvate thereof, or a solvate of such a salt.

In another aspect the invention provides a compound of formula (I) wherein $R^1$ is phenyl {optionally substituted (for example carrying 1 or 2 substituents) by halogen, hydroxy, cyano, $C_{1-4}$ alkyl (itself optionally mono-substituted by cyano, hydroxy or phenyl), $C_{1-4}$ alkoxy, $CF_3$, $OCF_3$, methylenedioxy, phenoxy (itself optionally substituted by halogen), tetrahydrofuranyloxy or tetrahydrofuranylmethoxy}, naphthyl, pyridinyl or tetrahydrothienyl.

In yet another aspect the present invention provides a compound of formula (I) wherein $R^1$ is phenyl {substituted (for example mono-substituted) by halogen, hydroxy, cyano, $C_{1-4}$ alkyl (itself optionally mono-substituted by cyano or hydroxy), $C_{1-4}$ alkoxy (for example methoxy), $CF_3$ or methylenedioxy} or tetrahydrothienyl.

In a still further aspect the present invention provides a compound of formula (I) wherein $R^1$ is phenyl {mono-substituted by halogen (for example chloro or fluoro), hydroxy, cyano, $C_{1-4}$ alkyl (mono-substituted by cyano), $CF_3$ or methylenedioxy} or tetrahydrothienyl.

Aminopyridinyl is, for example, 6-aminopyridin-3-yl. Aminothiazolyl is, for example, 2-aminothiazol-5-yl. 3-Azabicyclo[3.2.1]octyl is, for example, 3-azabicyclo[3.2.1]oct-8-yl.

In a further aspect the present invention provides a compound of formula (I) wherein $R^2$ is aminopyridine (for example 6-aminopyridin-3-yl).

The compounds of the present invention can be prepared by adaptation of methods described in the literature (for example WO 00/66557), or by using or adapting the methods of Examples 1, 26 or 51 below. It will be appreciated that when adapting methods of the literature or Examples 1, 26 or 51 functional groups of intermediate compounds may need to be protected by protecting groups. The preparations of certain intermediates are presented in Schemes 1 and 2.

For example a compound of formula (I) can be prepared by reacting a compound of formula (II):

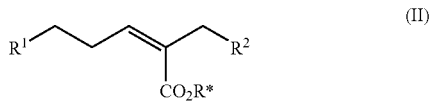

(II)

wherein $R^1$ is as defined above or includes a group that can be subsequently reacted to form the group $R^1$, $R^*$ is a suitable protecting group (such as a $C_{1-6}$ alkyl group (for example tert-butyl)) and $R^2$ is as defined above or the amine function of $R^2$ can be protected (for example by a tert-butoxycarbonyl group), with a thiol of formula L-SH, wherein L is a suitable protecting group (for example 4-methoxybenzyl), in the presence of a suitable catalyst (for example sodium hydride) and in a suitable solvent (for example N,N-dimethyl formamide) to form a compound of formula (III):

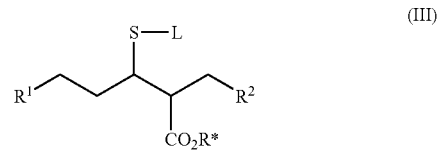

(III)

and, optionally reacting the functional group on $R^1$ (for example $R^1$ might include an acid group that can be coupled with an amino function to form an amide in the presence of a catalyst (such as HATU)), and subsequently removing the protecting groups as necessary.

Functional groups which it is desirable to protect include hydroxy, carboxylate and amino groups. Suitable protecting groups for hydroxy include trialkylsilyl or diarylalkyl-silyl (for example tert-butyldimethylsilyl, tert-butyldiphenylsilyl or trimethylsilyl), tetrahydropyranyl, methoxymethyl, benzyloxymethyl and 4-methoxybenzyl. Suitable protecting groups for carboxylate include ethyl, tert-butyl and benzyl esters. Suitable protecting groups for amino include tert-butyloxycarbonyl, 2,4,6-trimethoxybenzyl and benzyloxycarbonyl. The use of protecting groups is described in 'Protective Groups in Organic Synthesis', third edition, T. W. Greene & P. G. M. Wutz, Wiley-Interscience (1999). The protective group may also be a polymer resin such as Wang resin or a 2-chorotrityl chloride resin.

The compounds of the invention are inhibitors of carboxypeptidase U and are thus expected to be useful in those conditions where inhibition of carboxypeptidase U is beneficial, such as in the treatment or prophylaxis of thrombosis and hypercoagulability in blood and tissues, atherosclerosis, adhesions, dermal scarring, cancer, fibrotic conditions, inflammatory diseases and those conditions which benefit from maintaining or enhancing bradykinin levels in the body of mammals, such as man.

In a further aspect of the invention a compound of formula (I), or a pharmaceutically acceptable salt or solvate thereof, or a solvate of such a salt, is used in the in the treatment or prophylaxis of thrombosis. In another aspect of the invention a compound of formula (I), or a pharmaceutically acceptable salt or solvate thereof, or a solvate of such a salt, is used in method of manufacturing a medicament for the treatment or prophylaxis of thrombosis.

It is known that hypercoagulability may lead to thrombo-embolic diseases. Conditions associated with hypercoagulability and thrombo-embolic diseases which may be mentioned include protein C resistance and inherited or aquired deficiences in antithrombin III, protein C, protein S and heparin cofactor II. Other conditions known to be associated with hypercoagulability and thrombo-embolic disease include circulatory and septic shock, circulating antiphospholipid antibodies, hyperhomocysteinemia, heparin induced thrombocytopenia and defects in fibrinolysis. The compounds of the invention are thus indicated both in the therapeutic and/or prophylactic treatment of these conditions.

Other disease states which maybe mentioned include the therapeutic and/or prophylactic treatment of venous thrombosis and pulmonary embolism, arterial thrombosis (for example in myocardial infarction, unstable angina, thrombosis-based stroke and peripheral arterial thrombosis) and systemic embolism usually from the atrium during atrial fibrillation or from the left ventricle after transmural myocardial infarction.

The compounds of the invention are further indicated in the treatment of conditions where there is an undesirable excess of proCPU/CPU.

Moreover, the compounds of the invention are expected to have utility in prophylaxis of re-occlusion and restenosis (that is, thrombosis) after thrombolysis, percutaneous trans-luminal intervention (PTI) and coronary bypass operations; the prevention of re-thrombosis after microsurgery and vascular surgery in general.

Further indications include the therapeutic and/or prophylactic treatment of disseminated intravascular coagulation caused by bacteria, multiple trauma, intoxication or any other mechanism, fibrinolytic treatment when blood is in contact with foreign surfaces in the body, such as vascular grafts, vascular stents, vascular catheters, mechanical and biological prosthetic valves or any other medical device, and fibrinolytic treatment when blood is in contact with medical devices outside the body, such as during cardiovascular surgery using a heart-lung machine or in haemodialysis.

Furthermore, the compounds of the invention are expected to have utility in prophylaxis of atherosclerotic progression and transplant rejection in patients subject to organ transplantation, for example renal transplantation.

The compounds of the invention are also expected to have utility in inhibiting tumor maturation and progression.

Moreover, the compounds of the invention are expected to have utility in treatment of any condition in which fibrosis is a contributing factor. Such fibrotic conditions include cystic fibrosis, pulmonary fibrotic disease eg chronic obstructive pulmonary disease (COPD), adult respiratory distress syndrome (ARDS), fibromuscular dysplasia, fibrotic lung disease and fibrin deposits in the eye during opthalmic surgery.

The compounds of the invention are also expected to have utility in treatment of inflammation. In particular the invention may be used for the treatment or prevention of inflammatory diseases such as asthma, arthritis, endometriosis, inflammatory bowel diseases, psoriasis and atopic dermatitis.

The compounds of the invention are also expected to have utility in treatment of neurodegenerative diseases such as Alzheimers and Parkinsons.

The compounds of the invention are also expected to have utility in treatment of conditions known to benefit from maintaining or enhancing bradykinin levels. Such conditions include hypertension, angina, heart failure, pulmonary hypertension, renal failure and organ failure.

The compounds of the invention may also be combined and/or co-administered with any antithrombotic agent with a different mechanism of action, such as an anticoagulant (for example a vitamin K antagonist, an unfractionated or low molecular weight heparin, a synthetic heparin fragment such as fondaparinux, a thrombin inhibitor, a factor Xa inhibitor or other coagulation factor/enzyme inhibitor, a recombinant coagulation factor such as a recombinant human activated protein C) or an antiplatelet agent (such as acetylsalicylic acid, dipyridamole, ticlopidine, clopidogrel or other ADP-receptor [such as a P2Y12 or P2Y1] antagonist, a thromboxane receptor and/or synthetase inhibitor, a fibrinogen receptor antagonist, a prostacyclin mimetic or a phosphodiesterase inhibitor). The compounds of the invention may further be combined and/or coadministered with thrombolytics such as tissue plasminogen activator (natural, recombinant or modified), streptokinase, urokinase, prourokinase, anisoylated plasminogen-streptokinase activator complex (APSAC), animal salivary gland plasminogen activators, and the like, in the treatment of thrombotic diseases, in particular myocardial infarction, ischaemic stroke and massive pulmonary embolism.

The compounds of the invention should have a selectivity for carboxypeptidase U over carboxypeptidase N of >100:1, for example >1000:1, using the assay described below.

The inhibiting effect of the compounds of the present invention was estimated using the assay described in: Dirk Hendriks, Simon Scharpé and Marc van Sande, Clinical Chemistry, 31, 1936-1939 (1985); and Wei Wang, Dirk F. Hendriks, Simon S. Scharpé, The Journal of Biological Chemistry, 269, 15937-15944 (1994).

Thus, the present invention provides a compound of formula (I), or a pharmaceutically acceptable salt or solvate thereof, or a solvate of such a salt, as hereinbefore defined for use in therapy.

In a further aspect, the present invention provides the use of a compound of formula (I), or a pharmaceutically acceptable salt or solvate thereof, or a solvate of such a salt, as hereinbefore defined in the manufacture of a medicament for use in therapy.

In the context of the present invention, the term "therapy" includes "prophylaxis" unless there are specific indications to the contrary. The terms "therapeutic" and "therapeutically" should be understood accordingly.

The invention also provides a method of treating a condition where inhibition of carboxypeptidase U is beneficial in a mammal suffering from, or at risk of, said condition, which comprises administering to the mammal a therapeutically effective amount of a compound of formula (I), or a pharmaceutically acceptable salt or solvate thereof, or a solvate of such a salt, as hereinbefore defined.

For the above-mentioned therapeutic uses the dosage administered will vary with the compound employed, the mode of administration, the treatment desired and the disorder indicated.

The compounds of formula (I) and pharmaceutically acceptable salts, solvates or solvates of salts thereof may be used on their own but will generally be administered in the form of a pharmaceutical composition in which the formula (I) compound, salt, solvate or solvate of salt (active ingredient) is in association with a pharmaceutically acceptable adjuvant, diluent or carrier. Depending on the mode of administration, the pharmaceutical composition will, for example, comprise from 0.05 to 99% w (percent by weight), such as from 0.05 to 80% w, for example from 0.10 to 70% w, such as from 0.10 to 50% w, of active ingredient, all percentages by weight being based on total composition.

The present invention thus also provides a pharmaceutical composition comprising a compound of formula (I), or a pharmaceutically acceptable salt or solvate thereof, or a solvate of such a salt, as hereinbefore defined, in association with a pharmaceutically acceptable adjuvant, diluent or carrier.

The invention further provides a process for the preparation of a pharmaceutical composition of the invention which comprises mixing a compound of formula (I), or a pharmaceutically acceptable salt or solvate thereof, or a solvate of such a salt, as hereinbefore defined, with a pharmaceutically acceptable adjuvant, diluent or carrier.

Also included in the invention are derivatives of compounds of formula (I) which have the biological function of compounds of formula (I), such as prodrugs. Prodrugs are, for example, (pivaloyloxy)methyl esters and [(ethoxycarbonyl)oxy]methyl esters of carboxylic acids.

The following Examples illustrate the invention.

EXAMPLES

General Experimental Procedures

Mass spectra were recorded on a VG Platform II or a Micromass ZQ mass spectrometer equipped with an electrospray interface (LC-MS). High resolution mass spectra were recorded on a Micromass LCT mass spectrometer equipped with an electrospray interface (LC-HRMS). $^1$H NMR measurements were performed on Varian UNTIY plus 400, 500 and 600 spectrometers, operating at $^1$H frequencies of 400, 500 and 600 MHz respectively. NMR spectra were recorded in DMSO, $D_2O$, $CD_3CN$ or mixtures thereof. Chemical shifts are given in ppm with the solvent as internal standard. Chromatography separations were performed using Merck Silica gel 60 (0.063-0.200 mm). The compounds named below were named using ACD/Name version 6.06/11 Jun. 2002 available from advanced chemistry development inc., Canada.

Example 1

This Example illustrates the preparation of 2-[(6-aminopyridin-3-yl)methyl]-5-(1,1'-biphenyl-3-yl)-3-mercaptopentanoic acid (a) 3-(1,1'-Biphenyl-3-yl)propanal To a solution of 3-iodo-1,1'-biphenyl (0.964 g, 3.44 mmol) and tetrabutylammonium chloride (0.956 g, 3.44 mmol) in dry DMF (3 mL) was added alkyl alcohol (0.351 mL, 5.16 mmol), sodium hydrogencarbonate (0.723 g, 8.60 mmol), and palladium(II) acetate (31 mg, 0.14 mmol), and the mixture was stirred at room temperature for 18 h. The reaction mixture was then diluted with EtOAc and the solid material filtered off (Celite). The filtrate was washed with water three times, dried ($Na_2SO_4$) and concentrated. Flash chromatography (heptan/tert-butyl methyl ether, 4:1) of the residue gave 3-(1,1'-biphenyl-3-yl)propanal (0.601 g, 83%).

(b) tert-Butyl 5-(1,1'-biphenyl-3-yl)-2-({6-[(tert-butoxycarbonyl)amino]pyridin-3-yl}methyl)pent-2-enoate A solution of tert-butyl 3-{6-[(tert-butoxycarbonyl)amino]pyridin-3-yl}-2-(diethoxyphosphoryl)propanoate (1.058 g, 2.31 mmol) in dry THF (4 mL) was added to a solution of sodium hydride (0.111 g, 60% in mineral oil, 2.77 mmol) in dry TBF (3 mL) at 0° C. and the mixture was stirred at 0° C. for 60 min. To this mixture a solution of 3-(1,1'-biphenyl-3-yl)propanal (0.582 g, 2.77 mmol) in dry TBF (3 mL) was added, and the reaction mixture was allowed to attain room temperature over 22 h. EtOAc was then added, and the organic phase was washed with saturated aqueous $NH_4Cl$ and water, dried ($Na_2SO_4$) and concentrated. Flash chromatography (toluene/EtOAc, 15:1) of the residue gave tert-butyl 5-(1,1'-biphenyl-3-yl)-2-({6-[(tert-butoxycarbonyl)amino]pyridin-3-yl}methyl)pent-2-enoate (1.105 g, 93%) as a mixture of E/Z-isomers.

(c) tert-Butyl 5-(1,1'-biphenyl-3-yl)-2-({6-[(tert-butoxycarbonyl)amino]pyridin-3-yl}methyl)-3-[(4-methoxybenzyl)thio]pentanoate A solution of 4-methoxy-α-toluenethiol (0.58 mL, 4.17 mmol) in dry, degassed DMF (2 mL) was treated at room temperature with a catalytic amount of sodium hydride (60% in mineral oil), followed by a solution of tert-butyl 5-(1,1'-biphenyl-3-yl)-2-({6-[(tert-butoxycarbonyl)amino]pyridin-3-yl}methyl)pent-2-enoate (1.073 g, 2.08 mmol) in dry, degassed DMF (5 mL). After 20 h at room temperature the reaction mixture was diluted with EtOAc and washed with water three times. The organic layer was dried $Na_2SO_4$), concentrated, and subjected to flash chromatography (heptan/EtOAc, 3:1 and toluene/EtOAc 12:1) to give tert-butyl 5-(1,1'-biphenyl-3-yl)-2-({6-[(tert-butoxycarbonyl)amino]pyridin-3-yl}methyl)-3-[(4-methoxybenzyl)thio]pentanoate (1.251 g, 90%)

(d) 2-[(6-Aminopyridin-3-yl)methyl]-5-(1,1'-biphenyl-3-yl)-3-mercaptopentanoic acid tert-Butyl 5-(1,1'-biphenyl-3-yl)-2-({6-[(tert-butoxycarbonyl)amino]pyridin-3-yl}methyl)-3-[(4-methoxybenzyl)thio]pentanoate (0.669 g, 1.00 mmol) was dissolved in triethylsilane (0.75 mL) and trifluoroacetic acid (6.0 mL). The solution was heated to 60° C. for 3 h and then concentrated. Purification of the residue by reversed-phase HPLC (C-8 column, linear gradient 40%→100% of MeCN in 5% aqueous MeCN containing 0.15% trifluoroacetic acid) gave the title diastereomeric compound as the trifluoroacetic salt (0.342 g, 68%) after freeze-drying.

$^1$H NMR (400 MHz, $CD_3CN/D_2O$): δ 7.70 (dd,J=2.1, 9.2 Hz, 0.5H), 7.66 (dd,J=2.1, 9.2 Hz, 0.5 Hz), 7.61-7.58 (m, 2H), 7.53-7.51 (m, 1H), 7.46-7.41 (m, 4H), 7.38-7.32 (m, 2H), 7.22-7.16 (m, 1H), 6.88 (d,J=9.1 Hz, 0.5H), 6.84 (d,J=9.1 Hz, 0.5H), 3.10-2.74 (m, 6H), 2.17-2.04 (m, 1H), 1.91-1.78 (m, 1H). $^{13}$C NMR (101 MHz, $CD_3CN/D_2O$): δ 175.3, 174.9, 153.0, 146.0, 145.8, 142.3, 141.1, 140.9, 134.0, 133.9, 129.4, 129.2, 127.9, 127.9, 127.8, 127.3, 127.2, 127.1, 124.9, 124.8, 124.4, 124.1, 113.9, 113.8, 53.6, 53.0, 41.3, 40.5, 37.9, 33.1, 33.0, 31.2, 30.3. HRMS (ESI) calculated for $C_{23}H_{25}N_2O_2S$ 393.1637 (M+H)$^+$, found 393.1650.

Example 2

2-[(6-Aminopyridin-3-yl)methyl]-3-mercapto-5-(1-naphthyl)pentanoic acid was synthesised according to the procedure for Example 1.

$^1$H NMR (400 MHz, $CDCl_3$): δ 8.14-8.10 (d, 1H), 7.93-7.89 (d, 1H), 7.80-7.54 (m, 1H), 7.67-7.35 (m, 6H), 6.83-6.77 (m, 1H), 3.52-3.35(m, 1H), 3.22-3.12 (m, 2H), 2.90-2.80 (m, 3H), 2.25-2.13 (m, 1H), 2.05-1.87 (m, 1H). HRMS (ESI) calculated for $C_{21}H_{23}N_2O_2S$ 367.1480 (M+H)$^+$, found 367.1497.

Example 3

2-[(6-Aminopyridin-3-yl)methyl]-5-(3-cyanophenyl)-3-mercaptopentanoic acid was synthesised according to the procedure for Example 1.

$^1$H NMR (400 MHz, $CD_3CN/D_2O$): δ 7.73 (dd,J=2.2, 9.3 Hz, 0.5H), 7.70 (dd,J=2.2, 9.3 Hz, 0.5H), 7.58-7.40 (m, 5H), 6.90 (d,J=9.1 Hz, 0.5H), 6.88 (d,J=9.3 Hz, 0.5H), 2.99-2.88 (m, 2H), 2.82-2.71 (m, 4H), 2.12-2.00 (m, 1H), 1.88-1.74 (m, 1H).

$^{13}$C NMR (101 MHz, $CD_3CN/D_2O$): δ 175.5, 174.9, 153.0, 146.0, 145.8, 143.1, 133.9, 132.4, 132.3, 130.3, 130.3, 129.8, 124.3, 124.0, 119.4, 113.9, 113.9, 111.6, 53.8, 52.8, 41.1, 40.2, 37.4, 32.5, 32.5, 31.1, 30.5. HRMS (ESI) calcd for $C_{18}H_{20}N_3O_2S$ 342.1276 (M+H)$^+$, found 342.1277

Example 4

5-[3-(Aminocarbonyl)phenyl]-2-[(6-aminopyridin-3-yl)methyl]-3-mercaptopentanoic acid was synthesised according to the procedure for Example 1, starting from 3-iodo-N-(2,4,6-trimethoxybenzyl)benzamide. 3-iodo-N-(2,4,6-trimethoxybenzyl)benzamide was synthesised from 3-iodobenzoic acid using standard procedures.

¹H NMR (400 MHz, CD₃CN/D₂O): δ 7.72-7.67 (m, 1H), 7.65-7.61 (m, 2H), 7.52-7.49 (m,1H), 7.42-7.35 (m, 2H), 6.89 (d,J=9.3 Hz, 0.7H), 6.85 (d,J=9.1 Hz, 0.3H), 3.00-2.87 (m, 2H), 2.81-2.72 (m, 4H), 2.13-2.00 (m, 1H), 1.90-1.86 (m, 1H).
¹³C NMR (101 MHz, CD₃CN/D₂O): δ 175.7, 175.1, 171.5, 161.7, 161.4, 153.0, 146.0, 145.8, 142.1, 142.0, 133.9, 133.4, 132.7, 129.1, 127.8, 127.7, 125.5, 124.3, 124.0, 114.0, 113.9, 53.7, 52.6, 41.0, 39.9, 37.7, 37.6, 32.8, 32.7, 31.0, 30.4. HRMS (ESI) calcd for $C_{18}H_{22}N_3O_3S$ 360.1382 (M+H)⁺, found 360.1378.

Example 5

2-[(6-Aminopyridin-3-yl)methyl]-5-[2-fluoro4-(trifluoromethyl)phenyl]-3-mercaptopentanoic acid was synthesised according to the procedure for Example 1.
¹H NMR (400 MHz, CD₃CN/D₂O): δ 7.75-7.71 (m, 1H), 7.56 (d,J=1.6 H, 1H), 7.47-7.35 (m, 3H), 6.91 (d,J=9.3 Hz, 1 H),3.04-2.91 (m, 1H), 2.88-2.74 (m, 4H).
¹³C NMR (101 MHz, CD₃CN/D₂O): δ 175.4, 174.9, 162.0, 161.4, 159.6, 153.0, 146.0, 145.9, 134.0, 133.2, 133.0, 129.9, 124.2, 124.0, 121.4, 114.0, 113.9, 112.8, 112.6, 53.8, 53.0, 41.5, 40.8, 36.3, 36.2, 31.2, 30.6, 26.5. HRMS (ESI) calcd for $C_{18}H_{19}F_4N_2O_2S$ 403.1103 (M+H)⁺, found 403.1137.

Example 6

2-[(6-Aminopyridin-3-yl)methyl]-5-(3-chlorophenyl)-3-mercaptopentanoic acid was synthesised according to the procedure for Example 1.
¹H NMR (500 MHz, CD₃CN/D₂O): δ 7.75 (dd, 0.5H), 7.72 (dd, 0.5 H), 7.56 (d, 0.5H), 7.54 (d, 0.5 H), 7.30-7.10 (m, 4H), 6.92 (d, 0.5H), 6.91 (d, 0.5H), 3.02-2.65 (m, 6H), 2.10-2.00 (m, 1H), 1.88-1.74 (m, 1H). MS (ESI) 351.1 (M+H)⁺.

Example 7

2-[(6-Aminopyridin-3-yl)methyl]-5-(1,3-benzodioxol-5-yl)-3-mercaptopentanoic acid was synthesised according to the procedure for Example 1.
¹H NMR (400 MHz, CD₃CN/D₂O): δ 7.72(dd, 1H), 7.69 (d, 0.5H), 7.55 (s, 0.5H), 7.53 (s, 0.5H), 6.89 (m, 1H), 6.77-6.60 (m, 3H), 5.88(s, 2H), 3.0-2.70 (m, 5H), 2.58-2.68 (m, 1H), 1.92-2.08 (m, 1H), 1.69-1.81(m, 1H). HRMS (ESI) calculated for $C_{18}H_{20}N_2O_4S$ 361.1222 (M+H)⁺, found 361.1236.

Example 8

2-[(6-Aminopyridin-3-yl)methyl]-3-mercapto-5-pyridin-2-ylpentanoic acid was synthesised according to the procedure for Example 1, starting from 3-pyridin-2-ylpropanal.
¹H NMR (600 MHz, D₂O) δ ppm 1.90-2.37 (m, 2 H), 2.70-2.98 (m, 3 H), 3.05-3.11 (m, 1 H), 3.12-3.24 (m, 1 H), 3.32-3.41 (m, 1 H), 6.89 (d, 1 H), 7.57 (s, 1 H), 7.75 (dd, 1 H), 7.80-7.85 (m, 1 H), 7.88 (d, 1 H), 8.39-8.46 (m, 1 H), 8.54-8.60 (m, 1 H). MS (ESI) 318.2 (M+H)⁺.

Example 9

2-[(6-Aminopyridin-3-yl)methyl]-3-mercapto-5-(3,4,5-triethoxyphenyl)pentanoic acid was synthesised according to the procedure for Example 1.
¹H NMR (600 MHz, CD₃CN/D₂O) δ ppm 1.71-1.87 (m, 1H), 1.98-2.10 (m, 1H), 2.58-2.70 (m, 1H), 2.73-2.87 (m, 4H), 2.90 (d, 0.5H), 2.88-3.02 (m, 0.5H), 3.65 (s, 3H), 3.75 (s, 3H), 3.75 (s, 3H), 6.48 (s, 1H), 6.49 (s, 1H), 6.88 (d, 0.5H), 6.89 (d, 0.5H), 7.52 (d, 1H), 7.67-7.72 (m, 1H). MS (ESI) 407.2 (M+H)⁺.

Example 10

2-[(6-Aminopyridin-3-yl)methyl]-3-mercapto-5-pyridin-3-ylpentanoic acid was synthesised according to the procedure for Example 1, starting from 3-pyridin-3-ylpropanal.
¹H NMR (600 MHz, CD₃CN/D₂O) δ ppm 1.78-1.90 (m, 1H), 2.03-2.19 (m, 1H), 2.71-2.78 (m, 1H), 2.78-3.02 (m, 4H), 3.07-3.18 (m, 1H), 6.90 (d, 1H), 7.56 (s, 1H), 7.73-7.76 (m, 1H), 7.91-7.95 (m, 1H), 8.40-8.44 (m, 1H), 8.55-8.59 (m, 2H). MS (ESI) 318.2 (M+H)⁺.

Example 11

2-[(6-Aminopyridin-3-yl)methyl]-5-[4-(cyanomethyl)phenyl]-3-mercaptopentanoic acid was synthesised according to the procedure for Example 1.
¹H NMR (500 MHz, CD₃CN/D₂O): δ 7.99(dd, 0.5H), 7.96 (dd, 0.5H), 7.81 (d, 0.5H), 7.80 (d, 0.5H), 7.56-7.46 (m, 4H), 7.17 (d, 0.5H), 7.15 (d, 0.5H), 4.11 (s, 2H), 3.26-2.97 (m, 6H), 2.40-2.25 (m, 1H), 2.17-2.02 (m, 1H). MS (ESI) 356.2 (M+H)⁺.

Example 12

2-[(6-Aminopyridin-3-yl)methyl]-5-(2-hydroxyphenyl)-3-mercaptopentanoic acid was synthesised according to the procedure for Example 1, starting from 1-iodo-2-[(4-methoxybenzyl)oxy]benzene. 1-iodo-2-[(4-methoxybenzyl)oxy]benzene was synthesised from 2-iodophenol using standard procedures.
¹H NMR (500 MHz, 90% CD₃CN/D₂O) δ ppm 1.72-1.87 (m, 1 H), 2.00-2.15 (m, 1 H), 2.60-2.75 (m, 1 H), 2.77-2.94 (m, 4.6 H), 3.06-3.11 (m, 0.4 H), 6.75-6.81 (m, 2 H), 6.90-6.94 (m, 1H), 7.02-7.13 (m, 2 H), 7.56 (d,0.6 H), 7.57 (d, 0.4 H), 7.75 (dd, 0.6 H), 7.77 (dd, 0.4 H). MS (ESI) 333.2 (M+H)⁺.

Example 13

2-[(6-Aminopyridin-3-yl)methyl]-5-[4-(aminosulfonyl)phenyl]-3-mercaptopentanoic acid was synthesised according to the procedure for Example 1, starting from 4-iodo-N-(2,4,6-trimethoxybenzyl)benzenesulfonamide. 4-iodo-N-(2,4,6-trimethoxybenzyl)benzenesulfonamide was synthesised from 4-iodobenzenesulfonyl chloride using standard procedures.
¹H NMR (500 MHz, 75% CD₃CN/D₂O) δ ppm 1.79-1.92 (m, 1 H), 2.04-2.18 (m, 1 H), 2.76-2.88 (m, 4 H), 2.90-3.07 (m, 2 H), 6.92 (d, 0.5 H), 6.93 (d, 0.5 H), 7.40 (d, 1 H), 7.42 (d, 1 H), 7.57 (d, 0.5 H), 7.58 (d, 0.5 H), 7.72-7.81 (m, 3 H). MS (ESI) 396.1 (M+H)⁺.

Example 14

2-[(6-Aminopyridin-3-yl)methyl]-3-mercapto-5-(4-methoxyphenyl)pentanoic acid was synthesised according to the procedure for Example 1.
¹H NMR (500 MHz, 75% CD₃CN/D₂O) δ ppm 1.73-1.85 (m, 1 H), 1.99-2.11 (m, 1 H), 2.61-2.72 (m, 1 H), 2.75-2.95 (m, 4.5 H), 2.98-3.04 (m, 0.5 H), 3.75 (s, 1.5 H), 3.76 (s, 1.5 H), 6.82-6.88 (m, 2 H), 6.92 (d, 0.5 H), 6.93 (d, 0.5 H), 7.12

(d, 0.5 H), 7.15 (d, 0.5 H), 7.56 (s, 0.5 H), 7.58 (s, 0.5 ), 7.72-7.78 (m, 1 H). MS (ESI) 347.2 (M+H)+.

Example 15

2-[(6-Aminopyridin-3-yl)methyl]-5-(4-hydroxyphenyl)-3-mercaptopentanoic acid was synthesized from 2-[(6-aminopyridin-3-yl)methyl]-3-mercapto-5-(4-methoxyphenyl)pentanoic acid using standard conditions for the methoxy group hydrolysis (concentrated aqueous hydrochloric acid at reflux under argon for 24 h).

1H NMR (500 MHz, 25% $CD_3CN$ in $D_2O$) δ ppm 1.73-1.85 (m, 1 H), 1.94-2.09 (m, 1 H), 2.59-2.68 (m, 1 H), 2.75-2.87 (m, 4 H), 2.90 (d, 0.5 H), 2.98-3.03 (m, 0.5 H), 6.71-6.76 (m, 2 H), 6.90-6.95 (m, 1 H), 7.00-7.07 (m, 2 H), 7.54-7.57 (m, 1 H), 7.71-7.76 (m, 1 H). MS (ESI) 333.2 (M+H)+.

Example 16

2-[(6-Aminopyridin-3-yl)methyl]-3-mercapto-5-[4-(trifluoromethoxy)phenyl]-pentanoic acid was synthesised according to the procedure for Example 1.

$^1$H NMR (500 MHz, $CD_3CN/D_2O$) δ ppm 1.76-1.88 (m, 1 H), 2.01-2.14 (m, 1 H), 2.66-3.07 (m, 6 H), 6.94 (d, 1 H), 7.16-7.25 (m, 2 H), 7.26-7.34 (m, 2 H), 7.59 (d, 1 H), 7.78 (dd, 1 H). MS (ESI) 401.3 (M+H)+.

Example 17

2-[(6-Aminopyridin-3-yl)methyl]-5-(1,3-dimethyl-2,4-dioxo-1,2,3,4-tetrahydropyrimidin-5-yl)-3-mercaptopentanoic acid was synthesised according to the procedure for Example 1.

$^1$H NMR (500 MHz, $CD_3CN/D_2O$) δ ppm 1.57-1.76 (m, 1 H), 1.92-2.06 (m, 1 H), 2.31-2.45 (m, 1 H), 2.53-2.63 (m, 1 H), 2.75-3.07 (m, 4 H), 3.22 (s, 1.5 H), 3.23 (s, 1.5 H) 3.30 (s, 1.5 H), 3.30 (s, 1.5 H), 6.94 (d, 1 H), 7.30 (s, 0.5 H), 7.32 (s, 0.5 H), 7.59-7.64 (m, 1 H), 7.80 (dd, 1 H). MS (ESI) 379.2 (M+H)+.

Example 18

2-[(6-Aminopyridin-3-yl)methyl]-3-mercapto-5-(tetrahydro-2-thienyl)pentanoic acid was synthesised according to the procedure for Example 1, starting from 3-thien-2-ylpropanal.

$^1$H NMR (500 MHz, 90% $CD_3CN/D_2O$) δ ppm 1.48-1.60 (m, 3 H), 1.70-1.90 (m, 3 H), 2.00-2.10 (m,2 H), 2.70-3.10 (m, 6 H), 3.25-3.33 (m, 1 H), 6.92 (d, 1 H), 7.59 (s, 1 H), 7.78 (dd, 1 H). MS (ESI) 327.3 (M+H)+.

Example 19

2-[(6-Aminopyridin-3-yl)methyl]-5-[3-(hydroxymethyl)phenyl]-3-mercaptopentanoic acid was synthesised according to the procedure for Example 1, starting from 1-iodo-3-{[(4-methoxybenzyl)oxy]methyl}benzene. 1-iodo-3-{[(4-methoxybenzyl)oxy]methyl}benzene was synthesised from (3-iodophenyl)methanol using standard procedures.

$^1$H NMR (500 MHz, $CD_3CN/D_2O$) δ ppm 1.94-2.10 (m, 1 H), 2.21-2.37 (m, 1 H), 2.78-3.24 (m, 6 H), 4.77 (s, 1 H), 4.78 (s, 1 H), 7.09 (d, 0.5 H), 7.12 (d, 0.5 H), 7.34-7.44 (m, 3 H), 7.48-7.54 (m, 1 H), 7.73 (d, 0.5H), 7.74 (d, 0.5H), 7.91 (dd, 0.5H), 7.96 (dd, 0.5H). MS (ESI) 347.3 (M+H)+.

Example 20

2-[(6-Aminopyridin-3-yl)methyl]-5-[2-(2,4-dichlorophenoxy)phenyl]-3-mercaptopentanoic acid was synthesised according to the procedure for Example 1.

$^1$H NMR (400 MHz, $CDCl_3$): δ 7.64 (d, 1H), 7.51 (d, 1 H), 7.40 (d, 1H), 7.27 (m, 1H), 7.18-7.04 (m, 3H), 7.78-7.69 (m, 3H), 3.15-2.92(m, 2H), 2.87-2.65 (m, 4H),2.21-2.08 (m, 1H), 1.89-1.75 (m, 1H). HRMS (ESI) calculated for $C_{23}H_{22}Cl_2N_2O_3S$ 477.0806 (M+H)+, found 477.0170.

Example 21

2-[(6-Aminopyridin-3-yl)methyl]-5-(3,5dimethylphenyl)-3-mercaptopentanoic acid was synthesised according to the procedure for Example 1.

$^1$H NMR (500 MHz, $CD_3CN/D_2O$) δ ppm 1.72-1.85 (m, 1 H), 1.97-2.11(m, 1 H), 2.23 (s, 3 H), 2.24 (s, 3 H), 2.57-2.66 (m, 1 H), 2.75-2.87 (m, 4 H), 2.90 (d, 0.5 H), 2.99-3.05 (m, 0.5 H), 6.78-6.85 (m, 3 H), 6.88-6.94 (m, 1 H), 7.54 (d, 0.5 H), 7.56 (d, 0.5 H), 7.71 (dd, 0.5 H), 7.73 (d, 0.5 H). MS (ESI) 345.2 (M+H)+.

Example 22

2-[(6-Aminopyridin-3-yl)methyl]-3-mercapto-5-(4-propylphenyl)pentanoic acid was synthesised according to the procedure for Example 1.

$^1$H NMR (500 MHz, $CD_3CN/D_2O$) δ ppm 0.84 (t, 3 H), 1.49-1.58 (m, 2 H), 1.70-1.81 (m, 1 H), 1.96-2.04 (m, 1 H), 2.50 (t, 2 H), 2.60-2.70 (m, 1 H), 2.71-2.93 (m, 4 H), 2.93-3.01 (m, 1 H), 6.88 (d, 1 H), 7.07-7.10 (m, 4 H), 7.54 (d, 1 H), 7.71 (dd, 1 H). MS (ESI) 359.2 (M+H)+.

Example 23

2-[(6-Aminopyridin-3-yl)methyl]-5-(4-benzylphenyl)-3-mercaptopentanoic acid was synthesised according to the procedure for Example 1 starting from (4-iodophenyl)(phenyl)methanone.

$^1$H NMR (500 MHz, 80% $CD_3CN/D_2O$) δ ppm 1.72-1.82 (m, 1 H), 2.00-2.10 (m, 1 H), 2.72-2.62 (m, 1 H), 2.78-3.04 (m, 5H), 3.9 (s, 2 H), 6.90 (d, H), 7.08-7.29 (m, 9H), 7.55 (d, 1 H), 7.73 (dd, 1 H). HRMS (ESI) calculated for $C_{24}H_{27}N_2O_2S$ 407.1793 (M+H)+, found 407.1804.

Example 24

2-[(2-Amino-1,3-thiazol-5-yl)methyl]-3-mercapto-5-phenylpentanoic acid was synthesised according to the procedure for Example 1 starting from tert-butyl 3-{2-[(tert-butoxycarbonyl)amino]-1,3-thiazol-5-yl}-2-(diethoxyphosphoryl)propanoate. Tert-butyl 3-{2-[(tert-butoxycarbonyl)amino]-1,3-thiazol-5-yl}-2-(diethoxyphosphoryl)propanoate was synthesised as shown in Scheme 1.

$^1$H NMR (500 MHz, 90% $CD_3CN/D_2O$) δ ppm 1.78-1.90 (m, 1H), 2.00-2.11 (m, 1H), 2.68-2.77 (m, 1H), 2.78-3.2 (m, 4.5H), 3.05-3.11 (m, 0.5H), 6.85-6.88 (m, 1H), 7.16-7.33 (m, 5H). MS (ESI) 323.2 (M+H)+.

Example 25

2-(3-Azabicyclo[3.2.1]oct-8-ylmethyl)-3-mercapto-5-phenylpentanoic acid was synthesised according to the procedure for Example 1 starting from tert-butyl 8-[3-tert-butoxy-2-(diethoxyphosphoryl)-3-oxopropyl]-3-azabicyclo[3.2.1]octane-3-carboxylate. Tert-butyl 8-[3-tert-butoxy-2-(diethoxyphosphoryl)-3-oxopropyl]-3-azabicyclo[3.2.1]octane-3-carboxylate was synthesised as shown in Scheme 2.

$^1$H NMR (400 MHz, $CD_3CN/D_2O$): δ 7.90-7.80 (m, 2H), 7.80-7.70 (m, 3H), 3.80-3.60 (m, 2H), 3.60-3.35 (m, 4H), 3.35-3.18 (m, 1H), 3.18-3.00 (m, 1H), 2.90-1.80 (m, 11H). MS (ESI) 333.5 (M+H)+.

Example 26

This Example illustrates the preparation of 2-[(6-aminopyridin-3-yl)methyl]-3-mercapto-5-(3-{[methyl(2-phenylethyl)amino]carbonyl}phenyl)pentanoic acid.

(a) 3-{5-tert-butoxy-4-({6-[(tert-butoxycarbonyl)amino]pyridin-3-yl}methyl)-3-[(4-methoxybenzyl)thio]-5-oxopentyl}benzoic acid KOH (5 mL of a 1M solution in ethanol) was added to a solution of ethyl 3-{5-tert-butoxy-4-({6-[(tert-butoxycarbonyl)amino]pyridin-3-yl}methyl)-3-[(4-methoxybenzyl)thio]-5-oxopentyl}benzoate (0.27 g, 0.406 mmol, synthesised according to the procedure for Example 1) in ethanol (2 mL), and the mixture was stirred at room temperature for 2 h and then at 50° C. for 2 h. The reaction mixture was then diluted with diethyl ether and water. The organic phase was extracted with 0.1M aqueous KOH and the combined aqueous phase was acidified (pH 5) using 3M aqueous HCl. The aqueous phase was then extracted with diethyl ether and the organic phase was washed with brine, dried and concentrated. Purification of the residue by reversed-phase HPLC (C-8 column, linear gradient 40%→100% of MeCN in 5% aqueous MeCN containing 0.1 M ammonium acetate) gave a residue that was dissolved in toluene and water and concentrated to give 3-{5-tert-butoxy-4-({6-[(tert-butoxycarbonyl)amino]pyridin-3-yl}methyl)-3-[(4-methoxybenzyl)thio]-5-oxopentyl}benzoic acid (0.12 g, 54%).

(b) tert-butyl 2-({6-[(tert-butoxycarbonyl)amino]pyridin-3-yl}methyl)-3-[(4-methoxybenzyl)thio]-5-(3-{[methyl(2-phenylethyl)amino]carbonyl}phenyl)pentanoate N-methylphenethylamine (20 μL, 0.14 mmoL), HATU (55 mg, 0.15 mmoL) and iPr$_2$EtN (46 μL, 0.26 mmoL) was added to a solution of 3-{5-tert-butoxy-4-({6-[(tert-butoxycarbonyl) amino]pyridin-3-yl}methyl)-3-[(4-methoxybenzyl) thio]-5-oxopentyl}benzoic acid (84 mg, 0.132 mmol) in DMF (2 mL) under argon at 0° C. The reaction mixture was stirred for 2 h and was then quenched with ice. Diethylether and water was added and the aqueous phase was extracted diethyl ether. The combined organic phase was dried and concentrated. Flash chromatography (heptan/EtOAc, 3:1) gave tert-butyl 2-({6-[(tert-butoxycarbonyl)amino]pyridin-3-yl}methyl)-3-[(4-methoxybenzyl)thio]-5-(3-{[methyl(2-phenylethyl)amino]carbonyl}phenyl)pentanoate (81 mg, 81.4%).

(c) 2-[(6-aminopyridin-3-yl)methyl]-3-mercapto-5-(3{[methyl(2-phenylethyl)amino]carbonyl}phenyl)pentanoic acid tert-butyl 2-({6-[(tert-butoxycarbonyl)amino]pyridin-3-yl}methyl)-3-[(4-methoxybenzyl)thio]-5-(3-{[methyl(2-phenylethyl)amino]carbonyl}phenyl)pentanoate (80 mg, 0.106 mmol) was dissolved in triethylsilane (0.4 mL) and trifluoroacetic acid (3.0 mL). The solution was heated to 60° C. for 1 h and was then concentrated. Purification of the residue by reversed-phase HPLC (C-8 column, linear gradient 20%→100% of MeCN in 5% aqueous MeCN containing 0.15% trifluoroacetic acid) gave the title diastereomeric compound as the trifluoroacetic salt (64 mg, 100%) after freeze-drying.

$^1$H NMR (400 MHz, CD$_3$CN/D$_2$O): δ 7.76-6.63 (m, 12 H), 3.71 (m, 1H), 3.40 (m, 1H), 3.21-2.54 (m, 11H), 2.12-1.63 (m, 2H). HRMS (ESI) calcd for C$_{27}$H$_{31}$N$_3$O$_3$S 478.2164 (M+H)$^+$, found 478.2133.

Example 27

3-[5-(6-Aminopyridin-3-yl)-4-carboxy-3-mercaptopentyl]benzoic acid was synthesised according to the procedure for Example 26 starting from 3-{5-tert-butoxy-4-({6-[(tert-butoxycarbonyl)amino]pyridin-3-yl}methyl)-3-[(4-methoxybenzyl)thio]-5-oxopentyl}benzoic acid.

$^1$H NMR (400 MHz, D$_2$O): δ 8.05-8.01 (dd, 1H), 8.01-7.99 (s,1 H), 7.90-7.86 (dd, 1H), 7.73-7.70 (s, 1H), 7.68-7.58 (m, 2H), 7.08-7.04 (d, 1H), 3.18-3.08 (m, 1H), 3.06-2.90 (m, 5H), 2.36-2.26 (m, 1H), 2.14-2.04 (m, 1H). HRMS (ESI) calculated for C$_{18}$H$_{20}$N$_2$O$_4$S 361.1222 (M+H)$^+$, found 361.1212.

Example 28

2-[(6-Aminopyridin-3-yl)methyl]-5-[3-(3,4-dihydroisoquinolin-2(1H)-ylcarbonyl)phenyl]-3-mercaptopentanoic acid was synthesised according to the procedure for Example 26.

$^1$H NMR (500 MHz, CD$_3$CN/D$_2$O): δ 7.73 (m, 1H), 7.52 (s, 1H), 7.44-7.11 (m, 8H), 6.90 (m, 1H), 4.81 (s, 1H), 4.54 (s, 1H), 3.89 (br, 1H), 3.57 (br, 1H), 2.99-2.65 (m, 8H), 2.09 (m, 1H), 1.85 (m, 1H). HRMS (ESI) calcd for C$_{27}$H$_{29}$N$_3$O$_3$S 476.2008 (M+H)$^+$, found 476.2002.

Example 29

2-[(6-Aminopyridin-3-yl)methyl]-5-{3-[(6,7-dimethoxy-3,4-dihydroisoquinolin-2(1H)-yl)carbonyl]phenyl}-3-mercaptopentanoic acid was synthesised according to the procedure for Example 26.

$^1$H NMR (400 MHz, CD$_3$CN/D$_2$O): δ 7.68 (m, 1H), 7.49 (s, 1H), 7.38-7.22 (m, 4H), 6.90-6.72 (m, 2.5H), 6.47 (s, 0.5H), 4.69 (s, 1H), 4.44 (s, 1H), 3.96-3.46 (m, 8H), 3.01-2.59 (m, 8H), 2.17-1.67 (m, 2H). HRMS (ESI) calcd for C$_{29}$H$_{33}$N$_3$O$_5$S 536.2219 (M+H)$^+$, found 536.2248.

Example 30

2-[(6-Aminopyridin-3-yl)methyl]-3-mercapto-5-{3-[(2-pyridin-2-ylethoxy)carbonyl]phenyl}pentanoic acid was synthesised according to the procedure for Example 26.

$^1$H NMR (400 MHz, CD$_3$CN/D$_2$O): δ 8.64 (d, 1H), 8.46 (dd, 1H), 7.98 (d, 1H), 7.88 (dd, 1H), 7.77-7.64 (m, 3H), 7.58-7.31 (m, 3H), 6.89 (dd, 1H), 4.65 (t, 2H), 3.50 (t, 2H), 2.99-2.62 (m, 6H), 2.03 (m, 1H), 1.79 (m, 1H). HRMS (ESI) calcd for C$_{25}$H$_{27}$N$_3$O$_4$S 466.1803 (M+H)$^+$, found 466.1813.

Example 31

2-[(6-Aminopyridin-3-yl)methyl]-5-(3-{[2-(2,6-dichlorophenyl)ethoxy]carbonyl}phenyl)-3-mercaptopentanoic acid was synthesised according to the procedure for Example 26.

$^1$H NMR (400 MHz, CD$_3$CN/D$_2$O): δ 7.69 (m, 3H), 7.51 (s, 1H), 7.38-7.28 (m, 4H), 7.12 (m, 1H), 6.84 (m, 1H), 4.48 (m, 2H), 3.62 (m, 0.5H), 3.31 (m, 2H), 3.10 (m, 0.5H), 2.98-2.53 (m, 5H), 2.0 (m, 1H), 1.75 (m, 1H). HRMS (ESI) calcd for C$_{26}$H$_{26}$Cl$_2$N$_2$O$_4$S 533.1069 (M+H)$^+$, found 533.1071.

Example 32

2-[(6-Aminopyridin-3-yl)methyl]-5-[3-(ethoxycarbonyl) phenyl]-3-mercaptopentanoic acid was synthesised according to the procedure for Example 26 starting from ethyl 3-{5-tert-butoxy-4-({6-[(tert-butoxycarbonyl)amino]pyridin-3-yl}methyl)-3-[(4-methoxybenzyl)thio]-5-oxopentyl}benzoate.

$^1$H NMR (500 MHz, CD$_3$CN/D$_2$O): δ 7.90(d, 1H), 7.87 (s, 1H), 7.74 (d, 1H), 7.58 (s, 1H), 7.53 (d, 1H), 7.48 (t, 1H), 6.91 (d, 1H), 4.41 (q, 2H), 2.95-3.03 (m, 1H), 2.95-2.82 (m, 4H), 2.75-2.80 (m, 1H), 2.14-2.23 (m, 1H), 1.95-2.03 (m, 1H), 1.41 (t, 3H). HRMS (ESI) calculated for $C_{20}H_{25}N_2O_4S$ 389.1535 (M+H)$^+$, found 389.1555.

Example 33

2-[(6-Aminopyridin-3-yl)methyl]-5-(3-{[(2-fluoroethyl)amino]carbonyl}phenyl)-3-mercaptopentanoic acid was synthesised according to the procedure for Example 26.

$^1$H NMR (500 MHz, 10% CD$_3$CN in D$_2$O): δ 7.95 (dd, 0.5H), 7.90 (dd, 0.5 H), 7.86-7.81 (m, 2H), 7.75 (dd, 0.5H), 7.73 (dd, 0.5H), 7.70-7.60 (m, 2H), 7.13 (d, 0.5H), 7.07 (d, 0.5H), 4.89-4.86 (m, 1H), 4.8-4.76 (m, 1H), 3.91-3.94 (m, 1H), 3.85-3.89 (m, 1H), 3.25-3.12 (m, 2.5H), 3.11-2.98 (m, 3H), 2.92-2.97 (m, 0.5H), 2.41-2.24 (m, 1H), 2.21-2.01 (m, 1H). HRMS (ESI) calculated for $C_{20}H_{25}FN_3O_3S$ 406.1600 (M+H)$^+$, found 406.1560.

Example 34

2-[(6-Aminopyridin-3-yl)methyl]-5-{3-[(dimethylamino)carbonyl]phenyl}-3-mercaptopentanoic acid was synthesised according to the procedure for Example 26.

$^1$H NMR (500 Mz, 5% CD$_3$CN/D$_2$O): δ 7.77(dd, 0.5H), 7.72 (dd, 0.5H), 7.52-7.54 (m, 1H), 7.45-7.32 (m, 2H), 7.25-7.29 (m, 2H), 6.91 (d, 0.5H), 6.93 (d, 0.5H), 3.07 (s, 3H), 2.95 (two s, 3 H), 3.05-2.71 (m, 6H), 2.19-2.0 (m, 1H), 1.99-1.82 (m, 1H). HRMS (ESI) calculated for $C_{20}H_{26}N_3O_3S$ 388.1695 (M+H)$^+$, found 388.1683.

Example 35

2-[(6-Aminopyridin-3-yl)methyl]-3-mercapto-5-{3-[(vinylamino)carbonyl]phenyl}pentanoic acid was synthesised according to the procedure for Example 26.

$^1$H NMR (500 Mz, 10% CD$_3$CN/D$_2$O): δ 7.71(two dd, 1H), 7.53 (two dd, 0.5H), 6.89 (m, 1H), 6.77-6.60 (m, 3H), 5.88(s, 2H), 3.0-2.70 (m, 5H), 2.62 (m, 1H), 2.00 (m, 1H), 1.75(m, 1H). HRMS (ESI) calculated for $C_{20}H_{24}N_3O_3S$ 386.1538 (M+H)$^+$, found 386.1470.

Example 36

2-[(6-Aminopyridin-3-yl)methyl]-5-[3-({[2-(1,3-benzodioxol-5-yl)ethyl]amino}carbonyl)phenyl]-3-mercaptopentanoic acid was synthesised according to the procedure for Example 26.

$^1$H NMR (500 MHz, 20% CD$_3$CN/D$_2$O) δ ppm 1.88-2.06 (m, 1 H), 2.10-2.27 (m, 1 H), 2.79-3.11 (m, 8 H), 3.68 (t, 2 H), 6.00 (s, 2 H), 6.85 (m, 1 H), 6.90 (m, 2 H), 6.96 (d, 0.7 H), 7.01 (d, 0.3 H), 7.47 (m, 1.2H), 7.51 (m, 0.6 H), 7.56 (s, 0.7 H), 7.58 (s, 0.3 H), 7.62 (s, 2 H), 7.76 (d, 0.7 H), 7.81 (d, 0.3 H). HRMS (ESI) calculated for $C_{27}H_{29}N_3O_5S$ 508.1906 (M+H)$^+$, found 508.1935.

Example 37

2-[(6-Aminopyridin-3-yl)methyl]-5-{3-[(dibenzylamino)carbonyl]phenyl}-3-mercaptopentanoic acid was synthesised according to the procedure for Example 26.

$^1$H NMR (500 MHz, 50% CD$_3$CN/D$_2$O) δ ppm 2.28-2.40 (m, 1 H), 2.52-2.63 (m, 1 H), 3.25-3.53 (m, 6 H), 4.99 (s, 2 H), 5.23 (s, 2 H), 7.46 (d, 0.4 H), 7.48 (d, 0.6 H), 7.71 (d, 2 H), 7.83-8.00 (m, 12 H), 8.08 (s, 1 H), 8.25 (dd, 0.4 H), 8.28 (dd, 0.6 H). HRMS (ESI) calculated for $C_{32}H_{33}N_3O_3S$ 540.2321 (M+H)$^+$, found 540.2340.

Example 38

2-[(6-Aminopyridin-3-yl)methyl]-5-3-{[(2-hydroxyethyl)(methyl)amino]carbonyl}phenyl)-3-mercaptopentanoic acid was synthesised according to the procedure for Example 26.

$^1$H NMR (500 MHz, 50% CD$_3$CN/D$_2$O) δ ppm 1.71-2.11 (m, 2 H), 2.67-2.96 (m, 6 H), 2.89 (s, 1.5 H), 3.01 (s, 1.5 H), 3.34 (q, 1 H), 3.52-3.57 (m, 1 H), 3.59 (t, 1 H), 3.77 (t, 1 H), 6.74-6.86 (m, 1 H), 7.12-7.41 (m, 4 H), 7.45 (s, 1 H) 7.58-7.63 (m, 0.5 H), 7.65-7.69 (m, 0.5 H). HRMS (ESI) calculated for $C_{21}H_{28}N_3O_4S$ 418.1800 (M+H)$^+$, found 418.1752.

Example 39

2-[(6-Aminopyridin-3-yl)methyl]-5-{3-[(3-hydroxypyrrolidin-1-yl)carbonyl]phenyl}-3-mercaptopentanoic acid was synthesised according to the procedure for Example 26.

$^1$H NMR (400 MHz, CD$_3$CN/D$_2$O): δ 8.35-8.15 (m, 1H), 8.05 (br s, 1H), 8.00-7.75 (m, 4H), 7.50-7.35 (m, 1H), 6.16 (br m, 0.5H), 6.02 (br m, 0.5H), 5.02 (br m, 0.5H), 4.88 (br m, 0.5H), 4.50-3.60 (m, 4H), 3.55-3.20 (m, 7H), 3.0-2.2 (m, 4H). HRMS (ESI) calculated for $C_{22}H_{28}N_3O_4S$ 430.1829 (M+H)$^+$, found 430.1801.

Example 40

2-[(6-Aminopyridin-3-yl)methyl]-5-(3-{[4-(4-chlorophenyl)piperazin-1-yl]carbonyl}phenyl)-3-mercaptopentanoic acid was synthesised according to the procedure for Example 26.

$^1$H NMR (400 MHz, CD$_3$CN): δ 7.75-7.67 (m, 1H), 7.52-7.47 (dd, 1 H), 7.40-7.28(m, 5H), 7.12-7.07 (m, 3H), 6.90-6.84 (m, 1H), 4.00-3.50 (m, 4H), 3.40-3.20 (m, 4H), 3.03-2.90 (m, 1H), 2.87-2.70 (m, 5H), 2.17-2.03 (m, 1H),1.97-1.89 (m, 1H). HRMS (ESI) calculated for $C_{28}H_{31}ClN_4O_3S$ 539.1884 (M+H)$^+$, found 539.1868.

Example 41

2-[(6-Aminopyridin-3-yl)methyl]-5-3-{[benzyl(methyl)amino]carbonyl}phenyl)-3-mercaptopentanoic acid was synthesised according to the procedure for Example 26.

$^1$H NMR (400 MHz, CD$_3$CN): δ 7.75-7.18 (m, 11H), 6.88-6.80 (d, 1 H), 4.80-4.70 (s, 1H), 4.53-4.45 (s, 1H), 3.00-2.95 (m, 1H), 2.93-2.90 (s, 3H), 2.88-2.78 (m 5H), 2.05-2.00 (m 1H), 1.99-1.94 (m, 1H). HRMS (ESI) calculated for $C_{26}H_{29}N_3O_3S$ 464.2008 (M+H)$^+$, found 464.1972.

Example 42

2-[(6-Aminopyridin-3-yl)methyl]-3-mercapto-5-[3-(pyrrolidin-1-ylcarbonyl)phenyl]pentanoic acid was synthesised according to the procedure for Example 26.

$^1$H NMR (500 MHz, 95% CD$_3$CN in D$_2$O): δ 7.75 (dd, 0.5H), 7.69 (dd, 0.5 H), 7.51-7.54 (m, 1H), 7.44-7.30 (m, 4H), 6.91 (d, 0.5H), 6.87 (d, 0.5H), 3.53 (t, 2H), 3.30-3.40 (m, 2H), 3.00-2.79 (m, 5.5H), 2.67-2.74 (m, 0.5H), 2.18-1.8 (m, 6H). HRMS (ESI) calculated for $C_{22}H_{28}N_3O_3S$ 414.1851 (M+H)$^+$, found 414.1837.

Example 43

2-[(6-Aminopyridin-3-yl)methyl]-5-(3-{[4-(ethoxycarbonyl)piperidin-1-yl]carbonyl}phenyl)-3-mercaptopentanoic acid was synthesised according to the procedure for Example 26.

¹H NMR (500 MHz, CD$_3$CN/D$_2$O): δ 1.28 (t, 3H), 1.59-1.79 (m, 2H), 1.86-1.96 (m, 2H), 2.0-2.22 (m, 2H), 2.68-2.75 (m, 1H), 2.80-3.12 (m, 7H), 3.13-3.25 (m, 1H), 3.65 (d, 1H), 4.18 (q, 2H), 4.40-4.48 (m, 1H), 6.95-7.00 (m, 1H), 7.27-7.31 (m, 2H), 7.36-7.48 (m, 2H), 7.60 (s, 1H), 7.78 (dd, 0.5H), 7.82 (dd, 0.5H). HRMS (ESI) calculated for C$_{26}$H$_{34}$N$_3$O$_5$S 500.2219 (M+H)$^+$, found 500.2233.

Example 44

2-[(6-Aminopyridin-3-yl)methyl]-5-(3-{[4-hydroxymethyl)piperidin-1-yl]carbonyl}phenyl)-3-mercaptopentanoic acid was synthesised according to the procedure for Example 26.

¹H NMR (400 MHz, CD$_3$CN): δ 7.65-7.71 (dd, 1H), 7.49-7.52 (d, 1H), 7.18-7.36 (m, 4H), 6.82-6.85 (dd, 1H), 3.41-3.47 (m, 4H), 2.77-3.10 (m, 7H), 2.0-2.1 (m, 2H), 1.68-1.92 (m, 5H). HRMS (ESI) calculated for C$_{24}$H$_{32}$N$_3$O$_4$S 458.2114 (M+H)$^+$, found 458.2097.

Example 45

2-[(6-Aminopyridin-3-yl)methyl]-3-mercapto-5-{3-[(3-oxopiperazin-1-yl)carbonyl]phenyl}pentanoic acid was synthesised according to the procedure for Example 26.

¹H NMR (500 MHz, CD$_3$CN/D$_2$O) δ ppm 1.77-1.90 (m, 1H), 1.99-2.12 (m, 1H), 2.75-3.0 (m, 6H), 3.25-3.58 (m, 4H), 3.80-4.10 (m, 1H), 4.2 (s, 1H), 6.89 (d, 0.5H), 6.91 (d, 0.5H), 7.24-7.29 (m, 2H), 7.31-7.42 (m, 2H), 7.52 (s, 1H), 7.71 (dd, 0.4H), 7.74 (dd, 0.6H). HRMS (ESI) calculated for C$_{22}$H$_{27}$N$_4$O$_4$S 443.1753 (M+H)$^+$, found 443.1766.

Example 46

2-[(6-Aminopyridin-3-yl)methyl]-5-(3-{[benzyl(3-ethoxy-3-oxopropyl)amino]carbonyl}phenyl)-3-mercaptopentanoic acid was synthesised according to the procedure for Example 26.

¹H NMR (500 MHz, CD$_3$CN/D$_2$O) δ ppm 1.06 (t, 1H), 1.19 (t, 2H), 1.67-1.88 (m, 1H), 1.90-2.15 (m, 1H), 2.40-3.0 (m, 8H), 3.40-3.58 (m, 0.7H), 3.58-3.66 (m, 1.3H), 3.91 (q, 0.7H), 4.07 (q, 1.3H), 4.47 (s, 1.3H), 4.69 (s, 0.7H), 6.80-6.92 (m, 1H), 7.1-7.4 (m, 9H), 7.46 (s, 0.7H), 7.50 (s, 0.3H), 7.60-7.74 (m, 1H). HRMS (ESI) calculated for C$_{30}$H$_{36}$N$_3$O$_5$S 550.2376 (M+H)$^+$, found 550.2361.

Example 47

2-[(6-Aminopyridin-3-yl)methyl]-5-(3-{[(cyanomethyl)(methyl)amino]-sulfonyl}phenyl)-3-mercaptopentanoic acid was synthesised according to the procedure for Example 1, starting from N-(cyanomethyl)-3-iodo-N-methylbenzenesulfonamide. N-(cyanomethyl)-3-iodo-N-methylbenzenesulfonamide was synthesised from 3-iodobenzenesulfonyl chloride using standard procedures.

¹H NMR (500 MHz, CD$_3$CN/D$_2$O): δ 7.79 (dd, 0.5H), 7.76 (dd, 0.5H), 7.74-7.69 (m, 2H), 7.64-7.54 (m, 3H), 6.95 (d, 0.5H), 6.94 (d, 0.5H), 4.29 (s, 2H), 3.11-3.00 (m, 2H), 2.86 (s, 3H), 2.98-2.78 (m, 4H), 2.20-2.09 (m, 1H), 1.95-1.83 (m, 1H). HRMS (ES) calculated for C$_{20}$H$_{25}$N$_2$O$_4$S$_2$ 449.1317 (M+H)$^+$, found 449.1329.

Example 48

2-[(6-Aminopyridin-3-yl)methyl]-5-(3-{[(2S)-2-(anilinomethyl)pyrrolidin-1-yl]sulfonyl}phenyl)-3-mercaptopentanoic acid was synthesised according to the procedure for Example 1, starting from N-({(2S)-1-[(3-iodophenyl)sulfonyl]pyrrolidin-2-yl}methyl)aniline. N-({(2S)-1-[(3-iodophenyl)sulfonyl]pyrrolidin-2-yl}methyl)aniline was synthesised from 3-iodobenzenesulfonyl chloride using standard procedures.

¹H NMR (500 MHz, CD$_3$OD): δ 7.71 (dd, J=2.1, 9.1 Hz, 1H), 7.59-7.45 (m, 7H), 7.31-7.29 (m, 3H), 6.89 (d, J=9.3 Hz, 1H), 3.83-3.75 (m, 1H), 3.53 (ddd, J=3.1, 6.0, 13.0 Hz, 1H), 3.44-3.36 (m, 2H), 3.26-3.18 (m, 1H), 3.00-2.70 (m, 6H), 2.05-1.97 (m, 1H), 1.82-1.65 (m, 3H), 1.57-1.50 (m, 1H), 1.42-1.32 (m, 1H). HRMS (ESI) calculated for C$_{28}$H$_{34}$N$_4$O$_4$S$_2$ 555.2100 (M+H)$^+$, found 555.2032.

Example 49

2-[(6-Aminopyridin-3-yl)methyl]-3-mercapto-5-{3-[(methylamino)sulfonyl]-phenyl}pentanoic acid was synthesised according to the procedure for Example 1, starting from N-(2-furylmethyl)-3-iodo-N-methylbenzenesulfonamide. N-(2-furylmethyl)-3-iodo-N-methylbenzenesulfonamide was synthesised from 3-iodobenzenesulfonyl chloride using standard procedures.

¹H NMR (500 MHz, CD$_3$OD): δ 7.85 (dd, J=2.1, 9.1 Hz, 1H), 7.69-7.65 (m, 3H), 7.51-7.50 (m, 2H), 6.94 (dd, J =0.5, 9.1 Hz, 1H), 3.12-3.07 (m, 2H), 3.00-2.96 (m, 1H), 2.93-2.77 (m, 3H), 2.51 (s, 3H), 2.16-2.10 (m, 1H), 1.91-1.83 (m, 1H). HRMS (ESI) calculated for C$_{18}$H$_{23}$N$_3$O$_4$S$_2$ 410.1208 (M+H)$^+$, found 410.1207.

Example 50

2-[(6-Aminopyridin-3-yl)methyl]-3-mercapto-5-(3-{[methyl(2-phenylethyl)amino]sulfonyl}phenyl)pentanoic acid was synthesised according to the procedure for Example 1, starting from 3-iodo-N-methyl-N-(2-phenylethyl)benzenesulfonamide. 3-iodo-N-methyl-N-(2-phenylethyl)benzenesulfonamide was synthesised from 3-iodobenzenesulfonyl chloride using standard procedures.

¹H NMR (400 MHz, CDCl$_3$): δ 7.64 (s, 1H), 7.54-7.57 (d, 3H), 7.39-7.40 (d, 3H), 7.24-7.27 (t, 3H), 7.14-7.20 (m, 3H), 6.75 (s, 2H), 3.23-3.27 (t, 2H), 2.96-3.03 (m, 3H), 2.80-2.84 (t, 3H), 2.72 (s, 3H), 2.07 (s, 1H), 1.69-1.80 (dd, 1H), 1.53-1.55 (d, 1H). MS (ESI) 514.3 (M+H)$^+$.

Example 51

This Example illustrates the preparation of 2-[(6-aminopyridin-3-yl)methyl]-3-mercapto-5-[3-(tetrahydrofuran-3-yloxy)phenyl]pentanoic acid.

(a) tert-butyl(3-iodophenoxy)dimethylsilane

Imidazole (7.8 g, 115 mmol) was added to a solution of 3-iodophenol (12.7 g, 58 mmol) and tert-butyl(chloro)dimethylsilane (9.9 g, 65 mmol) in dichloromethane (80 mL) at 0° C. The reaction mixture was stirred at rt overnight. The suspension was washed three times with water and once with brine, dried and concentrated to give crude tert-butyl(3-iodophenoxy)dimethylsilane (20 g, 93%).

(b) tert-butyl 2-({6-[(tert-butoxycarbonyl)amino]pyridin-3-yl}methyl)-5-(3-hydroxyphenyl)-3-[(4-methoxybenzyl)thio]pentanoate Glacial acetic acid (190 μL, 3.3 mmoL) was added to a solution of tert-butyl 2-({6-[(tert-butoxycarbonyl)amino]pyridin-3-yl}methyl)-5-(3-{[tert-butyl(dimethyl)silyl]oxy}phenyl)-3-[(4-methoxybenzyl)thio]pentanoate (800 mg, 0.89 mmol, synthesised according to the procedure for Example 1, starting from tert-butyl(3-iodophenoxy)dimethylsilane) in dry THF (10 mL). Tetrabutylammonium fluoride trihydrate (489 mg, 1.5 mmol) was added and the mixture was stirred for 12 h at room temperature. EtOAc (150 mL) was added and the solution was washed with saturated aqueous NaHCO$_3$, water and brine, dried and concentrated. Flash chromatography (CH$_2$Cl$_2$/EtOAc, 10:1) gave tert-butyl 2-({6-[(tert-butoxycarbonyl)amino]pyridin-3-yl}methyl)-5-(3-hydroxyphenyl)-3-[(4-methoxybenzyl)thio]pentanoate (660 mg, 98%).

(c) tert-butyl 2-({6-[(tert-butoxycarbonyl)amino]pyridin-3-yl}methyl)-3-[(4-methoxybenzyl)thio]-5-[3-(tetrahydrofuran-3-yloxy)phenyl]pentanoate 1,1'-azobis(N,N-dimethylformamide)(134 mg, 0.78 mmol) was added to a solution of tri-n-butylphosphine (221 µL, 0.89 mmol) in toluene (2 mL). Tetrahydrofuran-3-ol (36 µL, 44 mmol) and tert-butyl 2-({6-[(tert-butoxycarbonyl)amino]pyridin-3-yl}methyl)-5-(3-hydroxyphenyl)-3-[(4-methoxybenzyl)thio]pentanoate (154 mg, 0.25 mmol) was added sequentially. The reaction mixture was stirred for 12 h at 80° C. Toluene (100 mL) was added and the mixture was washed with brine, dried and concentrated. Flash chromatography (toluene/EtOAc, 100:0 to 70:30) gave tert-butyl 2-({6-[(tert-butoxycarbonyl)amino]pyridin-3-yl}methyl)-3-[(4-methoxybenzyl)thio]-5-[3-(tetrahydrofuran-3-yloxy)phenyl]pentanoate (75 mg, 35%).

(d) 2-[(6-aminopyridin-3-yl)methyl]-3-mercapto-5-[3-(tetrahydrofuran-3-yloxy)phenyl]pentanoic acid 2-[(6-aminopyridin-3-yl)methyl]-3-mercapto-5-[3-(tetrahydrofuran-3-yloxy)phenyl]pentanoic acid was synthesised according to the procedure for Example 1, starting from tert-butyl 2-({6-[(tert-butoxycarbonyl)amino]pyridin-3-yl}methyl)-3-[(4-methoxybenzyl)thio]-5-[3-(tetrahydrofuran-3-yloxy)phenyl]pentanoate.

$^1$H NMR (500 MHz, CD$_3$CN/D$_2$O (1:1): δ 7.72 (dd, 1H), 7.53 (d, 1H), 7.22 (dd, 1H), 6.90 (d, 1H), 6.83 (d, 1H), 6.76-6.72 (m, 2H), 4.98 (m, 1H), 3.93-3.79 (m, 4H), 2.99-2.84 (m, 3H), 2.83-2.66 (m, 3H), 2.27-2.18 (m, 1H), 2.07-1.96 (m, 2H), 1.83-1.73 (m, 1H). HRMS (ESI) calculated for C$_{21}$H$_{27}$N$_2$O$_4$S 403.1692 (M+H)$^+$, found 403.1698.

Example 52

2-[(6-Aminopyridin-3-yl)methyl]-3-mercapto-5-[3-(tetrahydrofuran-3-ylmethoxy)-phenyl]pentanoic acid was synthesised according to the procedure for Example 51.

$^1$H NMR (400 MHz) CD$_3$CN): δ 7.75-7.69 (d, 1H), 7.58-7.56 (s, 1H), 7.25-7.18 (m, 1H), 6.88-6.75 (m, 4H), 3.98-3.58 (m, 6H), 3.10-3.00 (m, 1H), 2.95-2.82 (m, 3H), 2.74-2.65 (m, 2H), 2.13-2.03 (m, 1H), 1.98-1.66 (m, 4H). MS (ESI) 417.9 (M+H)$^+$.

Example 53

The activities of certain Examples in the assay described in: Dirk Hendriks, Simon Scharpé and Marc van Sande, Clinical Chemistry, 31, 1936-1939 (1985) are presented in Table I below.

TABLE I

| Example No. | IC$_{50}$ |
|---|---|
| 6 | 0.8 µM |
| 7 | 0.8 µM |
| 11 | 0.8 µM |
| 18 | 1.0 µM |

TABLE I-continued

| Example No. | IC$_{50}$ |
|---|---|
| 24 | 6.3 µM |
| 25 | 4.0 µM |
| 28 | 0.8 µM |
| 31 | 0.6 µM |
| 33 | 0.6 µM |
| 41 | 0.6 µM |
| 42 | 0.6 µM |
| 43 | 2.0 µM |
| 47 | 1.0 µM |

| Abbreviations | |
|---|---|
| HOAc = acetic acid | HOAc = acetic acid |
| MeOH = methanol | MeOH = methanol |
| min = minutes | min = minutes |
| rt = room temperature | rt = room temperature |
| DMF = dimethylformamide | TFA = trifluoroacetic acid |
| DMSO = dimethyl sulfoxide | THF = tetrahydrofuran |
| EtOAc = ethyl acetate | h = hour |
| DBU = 1,8-diazabicyclo[5.4.0]undec-7-ene | |
| HATU = O-(7-azabenzotriazol-1-yl)-N,N,N',N'-tetramethyluronium hexafluorophosphate | |

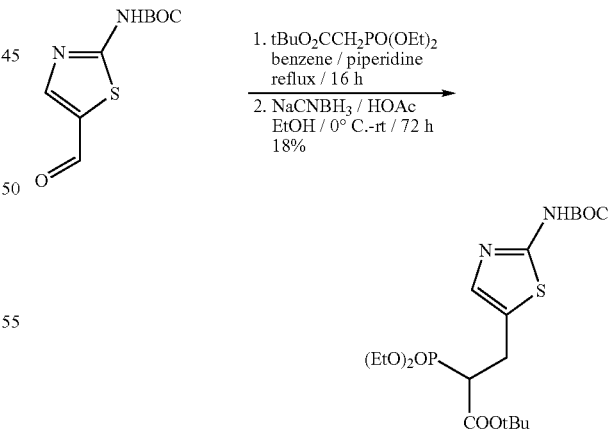

SCHEME 1

1. tBuO$_2$CCH$_2$PO(OEt)$_2$ benzene / piperidine reflux / 16 h
2. NaCNBH$_3$ / HOAc EtOH / 0° C.-rt / 72 h 18%

SCHEME 2

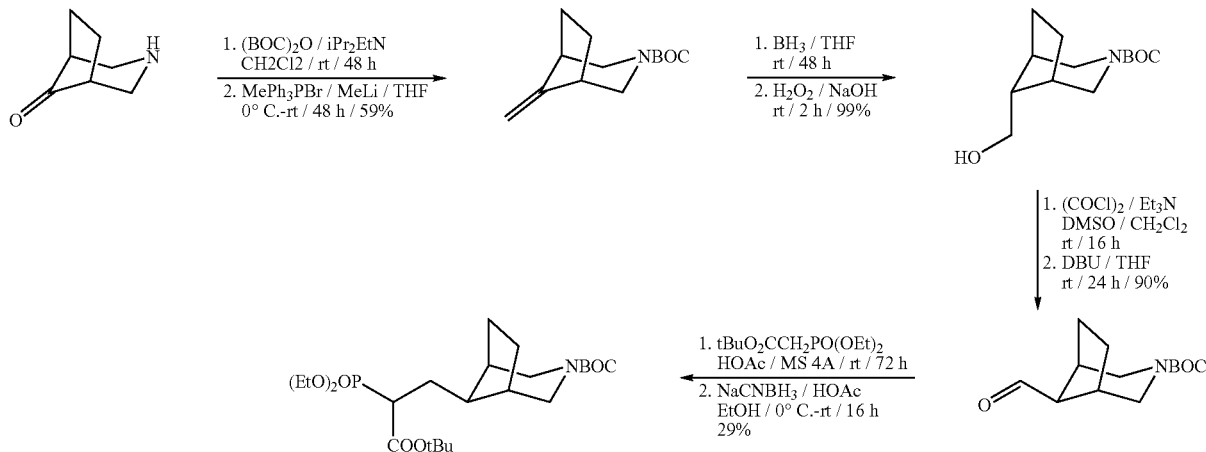

The invention claimed is:
1. A compound of formula (I):

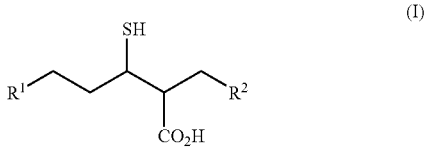

(I)

wherein:
R$^1$ is naphthyl, pyridinyl, 1,2,3,4-tetrahydropyrimidin-2,4-dione-yl, tetrahydrothienyl or phenyl, wherein said phenyl is substituted by 0, 1, 2 or 3 substituents selected from halogen, hydroxy, cyano, C$_{1-4}$ alkyl, C$_{1-4}$ alkoxy, CF$_3$, OCF$_3$, methylenedioxy, C(O)R$^3$, S(O)$_2$R$^4$, phenyl, phenoxy and tetrahydrofuranyloxy;
R$^2$ is aminopyridinyl, aminothiazolyl or 3-azabicyclo[3.2.1]octyl;
R$^3$ is hydroxy, C$_{1-4}$ alkoxy, NR$^5$R$^6$ or an N-linked 5- or 6-membered heterocyclic ring, wherein said N-linked 5- or 6-membered heterocyclic ring is substituted by 0, 1 or 2 substituents selected from hydroxy, oxo, C$_{1-4}$ alkyl, CO$_2$(C$_{1-4}$ alkyl) and phenyl;
R$^4$ is NR$^7$R$^8$ or an N-linked 5- or 6-membered heterocyclic ring, wherein said N-linked 5- or 6-membered heterocyclic ring is substituted by 0 or 1 substituent selected from hydroxy, oxo, C$_{1-4}$ alkyl, CO$_2$(C$_{1-4}$ alkyl) and phenyl; or fused to a benzene ring which is optionally substituted by 0, 1 or 2 substituents independently selected from C$_{1-4}$ alkoxy;
R$^5$, R$^6$, R$^7$ and R$^8$ are, independently, hydrogen, C$_{2-4}$ alkenyl or C$_{1-4}$ alkyl, wherein said C$_{1-4}$ alkyl is substituted by 0, 1 or 2 substituents selected from halogen, cyano, hydroxy, phenyl, pyridinyl, CO$_2$H or CO$_2$(C$_{1-4}$ alkyl);
provided that when R$^2$ is 6-aminopyridin-3-yl then R$^1$ is naphthyl, pyridinyl, 1,2,3,4-tetrahydropyrimidin-2,4-dione-yl, tetrahydrothienyl or phenyl, wherein said phenyl is substituted by 1, 2 or 3 substituents selected from halogen, hydroxy, cyano, C$_{1-4}$ alkyl, C$_{1-4}$ alkoxy, CF$_3$, OCF$_3$, methylenedioxy, C(O)R$^3$, S(O)$_2$R$^4$, phenyl, phenoxy and tetrahydrofuranoxy;
or a pharmaceutically acceptable salt thereof.

2. The compound of formula (I) as claimed in claim 1 wherein R$^1$ is pyridinyl, tetrahydrothienyl or phenyl, wherein said phenyl is substituted by 0, 1, 2 or 3 substituents selected from halogen, hydroxy, cyano, C$_{1-4}$ alkyl, C$_{1-4}$ alkoxy, CF$_3$, OCF$_3$, methylenedioxy, C(O)NH$_2$, S(O)$_2$NH$_2$ and phenyl.

3. A compound of formula (I) as claimed in claim 1 wherein R$^1$ is naphthyl, pyridinyl, tetrahydrothienyl or phenyl, wherein said phenyl is substituted by 0, 1, 2 or 3 substituents selected from halogen, hydroxy, cyano, C$_{1-4}$ alkyl, C$_{1-4}$ alkoxy, CF$_3$, OCF$_3$, methylenedioxy, phenoxy, tetrahydrofuranyloxy and tetrahydrofuranylmethoxy.

4. The compound of formula (I) as claimed in claim 1 wherein R$^1$ is tetrahydrothienyl or phenyl, wherein said phenyl is substituted by 0, 1, 2 or 3 substituents selected from halogen, hydroxy, cyano, C$_{1-4}$ alkyl, C$_{1-4}$ alkoxy, CF$_3$ and methylenedioxy.

5. The compound of formula (I) as claimed in claim 1, 2, 3 or 4 wherein R$^2$ is 6-aminopyridin-3-yl, 2-aminothiazol-5-yl or 3-azabicyclo[3.2.1]oct-8-yl.

6. A compound of formula (I) as claimed in claim 1, 2, 3 or 4 wherein R$^2$ is 6-aminopyridin3-yl.

7. A pharmaceutical formulation containing a compound according to claim 1 as active ingredient in combination with a pharmaceutically acceptable adjuvant, diluent or carrier.

8. A compound selected from
2-[(6-aminopyridin-3-yl)methyl]-5-(1,1'-biphenyl-3-yl)-3-mercaptopentanoic acid;
2-[(6-Aminopyridin-3-yl)methyl]-3-mercapto-5-(1-naphthyl)pentanoic acid;
2-[(6-Aminopyridin-3-yl)methyl]-5-(3-cyanophenyl)-3-mercaptopentanoic acid;
5-[3-(Aminocarbonyl)phenyl]-2-[(6-aminopyridin-3-yl)methyl]-3-mercaptopentanoic acid;
2-[(6-Aminopyridin-3-yl)methyl]-5-[2-fluoro-4-(trifluoromethyl)pheny]-3-mercaptopentanoic acid;
2-[(6-Aminopyridin-3-yl)methyl]-5-(3-chlorophenyl)-3-mercaptopentanoic acid;
2-[(6-Aminopyridin-3-yl)methyl]-5-(1,3-benzodioxol-5-yl)-3-mercaptopentanoic acid;
2-[(6-Aminopyridin-3-yl)methyl]-3-mercapto-5-pyridin-2-ylpentanoic acid;
2-[(6-Aminopyridin-3-yl)methyl]-3-mercapto-5-(3,4,5-triethoxyphenyl)pentanoic acid;

2-[(6-Aminopyridin-3-yl)methyl]-3-mercapto-5-pyridin-3-ylpentanoic acid;
2-[(6-Aminopyridin-3-yl)methyl]-5-[4-(cyanomethyl)phenyl]-3-mercaptopentanoic acid;
2-[(6-Aminopyridin-3-yl)methyl]-5-(2-hydroxyphenyl)-3-mercaptopentanoic acid;
2-[(6-Aminopyridin-3-yl)methyl]-5-[4-(aminosulfonyl)phenyl]-3-mercaptopentanoic acid;
2-[(6-Aminopyridin-3-yl)methyl]-3-mercapto-5-(4-methoxyphenyl)pentanoic acid;
2-[(6-Aminopyridin-3-yl)methyl]-5-(4-hydroxyphenyl)-3-mercaptopentanoic acid;
2-[(6-Aminopyridin-3-yl)methyl]-3-mercapto-5-[4-(trifluoromethoxy)phenyl]-pentanoic acid;
2-[(6-Aminopyridin-3-yl)methyl]-5-(1,3-dimethyl-2,4-dioxo-1,2,3,4-tetrahydropyrimidin-5-yl)-3-mercaptopentanoic acid;
2-[(6-Aminopyridin-3-yl)methyl]-3-mercapto-5-(tetrahydro-2-thienyl)-pentanoic acid;
2-[(6-Aminopyridin-3-yl)methyl]-5-[3-(hydroxymethyl)phenyl]-3-mercaptopentanoic acid;
2-[(6-Aminopyridin-3-yl)methyl]-5-[2-(2,4-dichlorophenoxy)phenyl]-3-mercaptopentanoic acid;
2-[(6-Aminopyridin-3-yl)methyl]-5-(3,5-dimethylphenyl)3-mercaptopentanoic acid;
2-[(6-Aminopyridin-3-yl)methyl]-3-mercapto-5-(4propylphenyl)pentanoic acid;
2-[(6-Aminopyridin-3-yl)methyl]-5-4-benzylphenyl)-3-mercaptopentanoic acid;
2-[(2-Amino-1,3-thiazol-5-yl)methyl]-3-mercapto-5-phenylpentanoic acid;
2-(3-Azabicyclo[3.2.1]oct-8-ylmethyl)-3-mercapto-5-phenylpentanoic acid;
2-[(6-aminopyridin-3-yl )methyl]-3-mercapto-5-(3-{[methyl(2-phenylethyl)amino]carbonyl}phenyl)pentanoic acid;
3-[5-(6-Aminopyridin-3-yl)-4-carboxy-3-mercaptopentyl]benzoic acid;
2-[(6-Aminopyridin-3-yl)methyl]-5-[3-(3,4-dihydroisoquinolin-2(1H)-ylcarbonyl)phenyl]-3-mercaptopentanoic acid;
2-[(6-Aminopyridin-3-yl)methyl]-5-{3-[(6,7-dimethoxy-3,4-dihydroisoquinolin-2(1H) -yl)carbonyl]phenyl}-3-mercaptopentanoic acid;
2-[(6-Aminopyridin-3-yl)methyl]-3-mercapto-5-{3-[(2-pyridin-2-ylethoxy)carbonyl]phenyl}pentanoic acid;
2-[(6-Aminopyridin-3-yl)methyl]-5-(3-{[2-(2,6-dichlorophenyl)ethoxy]carbonyl}phenyl)-3-mercaptopentanoic acid;
2-[(6-Aminopyridin-3-yl)methyl]-5-[3-(ethoxycarbonyl)phenyl]-3-mercaptopentanoic acid;
2-[(6-Aminopyridin-3-yl)methyl]-5-(3-{[(2-fluoroethyl)amino]carbony-1}phenyl)-3-mercaptopentanoic acid;
2-[(6-Aminopyridin-3-yl)methyl]-5-{3-[(dimethylamino)carbonyl]phenyl}-3-mercaptopentanoic acid;
2-[(6-Aminopyridin-3-yl)methyl]-3-mercapto-5-{3-[(vinylamino)carbonyl]phenyl}pentanoic acid;
2-[(6-Aminopyridin-3-yl)methyl]-5-[3-({[2-(1,3-benzodioxol-5-yl)ethyl]amino}carbonyl)phenyl]-3-mercaptopentanoic acid;
2-[(6-Aminopyridin-3-yl)methyl]-5-{3-[(dibenzylamino)carbonyl]phenyl}-3-mercaptopentanoic acid;
2-[(6-Aminopyridin-3-yl)methyl]-5-3-{[(2-hydroxyethyl)(methyl)amino]carbonyl}phenyl)-3-mercaptopentanoic acid;
2-[(6-Aminopyridin-3-yl)methyl]-5-{3-[(3-hydroxypyrrolidin-1-yl)carbonyl]phenyl}-3-mercaptopentanoic acid;
2-[(6-Aminopyridin-3-yl)methyl]-5-(3-{[4-(4-chlorophenyl)piperazin-1-yl]carbonyl}phenyl)-3-mercaptopentanoic acid;
2-[(6-Aminopyridin-3-yl)methyl]-5-3-{[benzyl(methyl)amino]carbonyl}phenyl)-3-mercaptopentanoic acid;
2-[(6-Aminopyridin-3-yl)methyl]-3-mercapto-5-[3-(pyrrolidin-1-ylcarbonyl)phenyl]pentanoic acid;
2-[(6-Aminopyridin-3-yl)methyl]-5-(3-{[4-(ethoxycarbonyl)piperidin-1-yl]carbonyl}phenyl)-3-mercaptopentanoic acid;
2-[(6-Aminopyridin-3-yl)methyl]-5-(3-{[4-hydroxymethyl)piperidin-1-yl]carbonyl}phenyl)-3-mercaptopentanoic acid;
2-[(6-Aminopyridin-3-yl)methyl]-3-mercapto-5-{3-[(3-oxopiperazin-1-yl)carbonyl]phenyl)pentanoic acid;
2-[(6-Aminopyridin-3-yl)methyl]-5-(3-{[benzyl(3-ethoxy-3-oxopropyl)amino]carbonyl}phenyl)-3-mercaptopentanoic acid;
2-[(6-Aminopyridin-3-yl)methyl]-5-(3-{[(cyanomethyl)(methyl)amino]sulfonyl}phenyl)-3-mercaptopentanoic acid;
2-[(6-Aminopyridin-3-yl)methyl]-5-(3-{[(2S)-2-(anilinomethyl)pyrrolidin-1-yl]sulfonyl}phenyl)-3-mercaptopentanoic acid;
2-[(6-Aminopyridin-3-yl)methyl]-3-mercapto-5-{3-[(methylamino)sulfonyl]-phenyl}pentanoic acid;
2-[(6-Aminopyridin-3-yl)methyl]-3-mercapto-5-(3-{[methyl(2-phenylethyl)amino]sulfonyl}phenyl)pentanoic acid;
2-[(6-aminopyridin-3-yl)methyl]-3-mercapto-5-[3-(tetrahydrofuran-3-yloxy)phenyl]pentanoic acid; and
2-[(6-Aminopyridin-3-yl)methyl]-3-mercapto-5-[3-(tetrahydrofuran-3-ylmethoxy)-phenyl]pentanoic acid,
or a pharmaceutically acceptable salt thereof.

\* \* \* \* \*